United States Patent [19]
Obrecht et al.

[11] 3,968,178
[45] July 6, 1976

[54] CHLORINATION OF HYDROCARBONS

[75] Inventors: Robert P. Obrecht, New Canaan; Marlin J. Bennett, Ridgefield, both of Conn.

[73] Assignee: Stauffer Chemical Company, Westport, Conn.

[22] Filed: Oct. 19, 1971

[21] Appl. No.: 190,640

Related U.S. Application Data

[63] Continuation of Ser. No. 726,804, May 6, 1968, abandoned, which is a continuation-in-part of Ser. No. 681,546, Nov. 8, 1967, abandoned.

[52] U.S. Cl. ............... 260/658 R; 260/654 A; 260/659 A; 260/657; 260/662 R; 260/664; 423/481; 423/488
[51] Int. Cl.² ..................... C07C 17/10
[58] Field of Search ........... 260/662 R, 657, 664, 260/658 R, 654 H; 423/481, 488

[56] References Cited
UNITED STATES PATENTS

| 2,334,033 | 11/1943 | Riblett | 260/662 |
| 2,406,195 | 8/1946 | Cass | 260/657 |
| 2,807,656 | 9/1957 | Cherniavsky | 260/662 R |
| 2,862,980 | 12/1958 | Muench et al. | 260/651 HA |
| 2,942,039 | 6/1960 | Allen et al. | 260/662 R |
| 2,989,571 | 5/1958 | Eisenlohr | 260/662 R |
| 3,126,419 | 3/1964 | Burks et al. | 260/658 R |
| 3,304,337 | 2/1967 | Jordan et al. | 260/658 R |
| 3,502,734 | 3/1970 | Baird et al. | 260/658 R |

FOREIGN PATENTS OR APPLICATIONS

| 517,009 | 9/1955 | Canada | 260/659 A |
| 695,297 | 9/1964 | Canada | 260/659 A |

Primary Examiner—James O. Thomas, Jr.
Assistant Examiner—Nicky Chan
Attorney, Agent, or Firm—Daniel S. Ortiz

[57] ABSTRACT

The invention is a process for the thermal substitution chlorination of methyl chloride at an elevated pressure and separation of the chlorinated hydrocarbons from the anhydrous hydrogen chloride by partial condensation at an elevated pressure to provide a hydrogen chloride gas stream containing only small quantities of chlorinated hydrocarbons.

8 Claims, 1 Drawing Figure

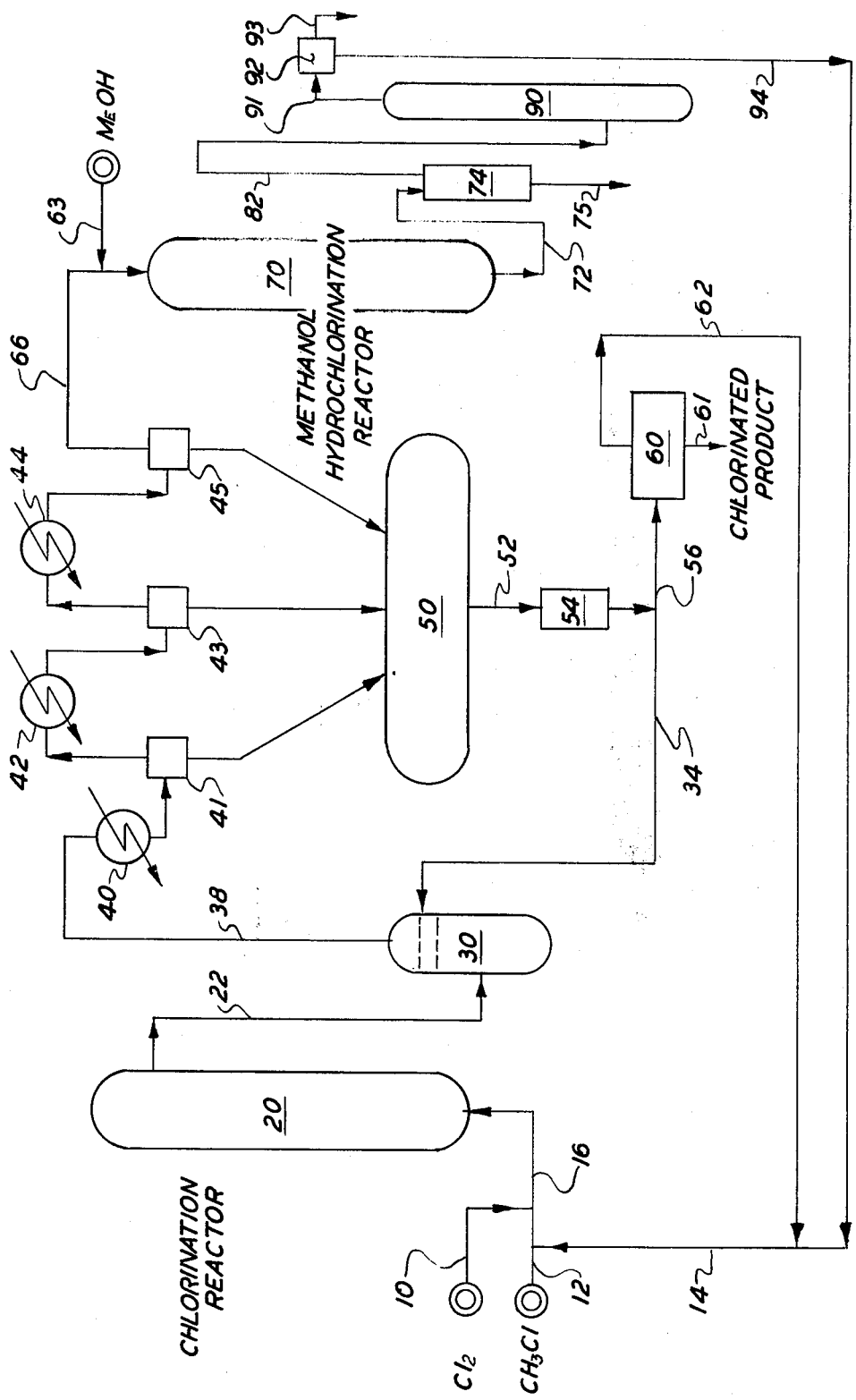

CHLORINATION OF HYDROCARBONS

CROSS-REFERENCES TO RELATED APPLICATIONS

This application is a continuation of application Ser. No. 726,804, filed May 6, 1968, now abandoned, which is a continuation-in-part of application Ser. No. 681,546, filed Nov. 8, 1967, now abandoned.

This invention relates to the recovery of substantially pure and anhydrous hydrogen chloride from the effluent of certain organic substitution chlorination reactions. More particularly, this invention relates to an efficient and economically attractive process for carrying out organic substitution chlorination reaction under elevated pressures in which the hydrogen chloride produced is recovered in the substantially pure state and under anhydrous conditions thus being suitable for utilization in hydrogen chloride consuming reactions, such as oxychlorination and alcohol hydrochlorination reactions. In one preferred aspect, this invention relates to a novel and highly efficient integrated process involving a methyl chloride partial chlorination reaction and a methanol hydrochlorination reaction employing substantially anhydrous hydrogen chloride recovered from the partial chlorination process.

Commercial partial substitution chlorination processes usually employ reaction conditions and reactor design principles which ensure substantially complete reaction of the chlorine which is fed to the reaction system. One such process is described in U.S. Pat. No. 3,126,419. In that process an excess of the hydrocarbon and/or the partially chlorinated hydrocarbon is used under thermal vapor phase substitution chlorination reaction conditions. The reactor system yields a vaporous effluent which contains the desired chlorinated products in admixture with by-product hydrogen chloride and unreacted hydrocaron and/or partially chlorinated hydrocarbon raw material. Such vapor phase organic chlorination reactions are usually conducted with anhydrous feed materials since the equipment required for anhydrous reaction and subsequent recovery of the product is considerably more economical to install, maintain and operate than the equipment required for systems tolerant of water or hydrochloric acid in the liquid phase. In commercial operations involving organic substitution chlorination reactions, although anhydrous reaction conditions are employed, every known installation employs wet hydrogen chloride absorption often followed by hydrogen chloride stripping and drying to obtain a useable and pure form of hydrogen chloride by-product. This recovery procedure simultaneously permits recovery, and recycle, if desired, of preferably only one of the unreacted feed materials or of any substitution chlorination product. Unfortunately, the wet hydrogen chloride recovery system is expensive in its construction, operation and maintenance. It is, therefore, the principal object of the present invention to overcome and eliminate the inherent deficiencies and disadvantages of prior processes for recovering hydrogen chloride from organic substitution chlorination reactions.

An object of the present invention is to provide a process for recovering substantially anhydrous hydrogen chloride from organic substitution chlorination reactions.

Another object of the present invention is to recover substantially anydrous and purified hydrogen chloride under an elevated pressure from the effluent of an organic substitution chlorination reaction.

Another object is to provide economically attractive and efficient processes in which hydrogen chloride by-product from organic substitution chlorination reactions can efficiently be recovered in a substantially anhydrous and purified state for reutilization in hydrogen chloride consuming reactions, such as, e.g, hydrochlorination and oxychlorination reactions.

Another object of the present invention is to provide an economically attractive integrated process including the partial chlorination of methyl chloride and the hydrochlorination of methanol.

Still another object of the present invention is to provide an economically attractive method for the recovery of hydrogen chloride in an anhydrous and essentially purified state from the effluent of an organic substitution chlorination reaction in a manner such that the conventional wet hydrogen chloride absorption-stripping system is avoided.

Other objects and advantages inherent in the present invention will become apparent from the following description and disclosure.

These and other objects are generally accomplished in accordance ith the present invention by carying out an organic substitution chlorination reaction under an elevated pressure and substantially anhydrous conditions to produce an effluent containing the desired chlorinated products admixed with unreacted raw materals and hydrogen chloride by-product. The reaction effluent is then passed to a recovery zone operated under an elevated pressure and relatively low terminal temperature to separate a substantially anhydrous hydrogen chloride stream from which a large percentage of the chlorinated materials have been removed. The chlorinated products are then recovered by any appropriate and suitable method and means while the substantially anhydrous hydrogen chloride is conveyed to a suitable hydrogen chloride consuming reaction zone.

The process of the present invention which involves the recovery of essentially purified and anhydrous hydrogen chloride from the effluent of organic substitution chlorination reactions will be understood by those skilled in the art to be applicable to a wide variety of such substitution chlorination reactions and their combination with hydrogen chloride consuming reactions. Such substitution chlorination reactions include the reactions of chlorine with compounds in the class of those formed by saturated aliphatic hydrocarbons containing 1 to 20 carbon atoms, e.g., methane, ethane and propane, and halogen substituted $C_1$ to $C_{20}$ hydrocarbons, such as e.g., methyl chloride, methylene chloride and chloroform.

The substantially anhydrous hydrogen chloride containing a low percentage of chlorinated materials which is recovered under an elevated pressure can be utilized without conpression or further purification in an alcohol hydrochlorination process, e.g., the hydrochlorination of methanol or ethanol. Such material can also be used as feed to a suitable oxychlorination process. Additional purification of the substantially anhydrous hydrogen chloride to remove chlorinated materials therefrom makes such substantially anhydrous, purified hydrogen chloride suitable for use in a wide variety of processes wherein such hydrogen chloride is required. Such processes include the oxychlorination of saturated as well as unsaturated aliphatic hydrocarbons, partially halogenated derivatives thereof, and aromatic compounds including but not limited to the oxychlorination of ethylene, propylene, butylene, ethylene dichloride, methane, acetylene, benzene, methyl chloride, ethyl chloride, trichloroethanes and tetrachloroethanes. The substantially anhydrous, purified hydrogen chloride is further utilized in the aldehyde consuming chloromethylation of lower alkyl substituted benzenes, e.g., toluene. Such chloromethylation is a Friedel Craft reaction wherein a chloroalkyl group is introduced into an aromatic ring in the presence of strong hydrochloric acid.

In one preferred embodiment of the process of the present invention an alkyl chloride substitution chlorination reaction is operated under an elevated pressure and temperature to produce desired chlorinated hydrocarbon products and byproduct hydrogen chloride. The substitution chlorination reaction is operated under an elevated pressure of at least about 5 psig and, preferably, at an elevated pressure of at least about 50 psig. A most preferable range of pressures is between about 50 psig and about 200 psig. The substitution chlorination reaction effluent is separated in a partial condensation zone operated under an elevated pressure and anhydrous conditions to recover an anhydrous hydrogen chloride, non-condensable vent gas containing only a small percentage of unreacted alkyl chloride. This gaseous material can be conveyed to an alcohol hydrochlorination reaction zone without the need for further compression while operating the alcohol hydrochlorination zone under efficient reaction conditions. One most preferred combination comprises an integrated process including partial chlorination of methyl chloride to obtain methylene chloride and/or chloroform and utilization of the substantially anhydrous hydrogen chloride derived therefrom in a methanol hydrochlorination plant to produce methyl chloride. The methyl chloride produced in the hydrochlorination reaction is, at least in part, fed to the partial chlorination process.

Having thus described the invention in general terms reference is now made to the FIGURE of the drawing which illustrates, diagrammatically, one preferred embodiment of the process of the present invention which should not be construed as unduly limiting thereof.

Referring to the drawing, chlorine vapor in line 10, methyl chloride vapor in line 12 and/or vaporous recycle material containing methyl chloride in line 14 are intimately mixed and passed in line 16 to chlorination reactor 20. Chlorination reactor 20 is maintained under an elevated presure e.g. at least above about 5 psig. Suitable conditions are maintained in the chlorination reactor 20 to effect substitution chlorination of the methyl chloride to methylene chloride and/or chloroform. Preferably the reaction is effected thermally in the absence of a catalyst at a temperature between about 350° and about 500°C. It is understood, however, that this invention is not limited by the particular manner of carrying out the substitution chlorination reaction which also can be effected in the presence of a catalyst, by photochemical initiation or by gamma radiation initiation. Liquid phase as well as gas phase reaction conditions can be employed. One essential element, however, is that the chlorination reaction be carried out under substantially anhydrous conditions.

The reaction effluent in line 22 contains unreacted $CH_3Cl$, $CH_2Cl_2$, $CHCl_3$, $CCl_4$ and by-product HCl. Gaseous material in line 22, at an elevated temperature and pressure, is introduced to quench tank 30 in which the effluent is contacted with relatively cool reflux material introduced from line 34. Quench column 30, is employed in the process to desuperheat the reactor effluent and to prevent solid by-product carryover from reaching the heat exchangers employed in the recovery system. Any suitable gas-liquid contacting means, e.g., a multisieve plate column, can be employed in the operation of zone 30.

Substantially cooled vapor still under an elevated pressure, is withdrawn in line 38 and passed to a partial condensation zone, which in this embodiment is represented by a series of condensers, 40, 42 and 44 and gas-liquid separators, 41, 43 and 45. It is to be understood that any suitable method and means for effecting partial condensation can be employed at this point in the process. In the preferred embodiment, condensor 40 employs water as the coolant material while condensers 42 and 44, operated at successively lower temperatures, employ suitable refrigerant cooling materials. The runoff from the gas-liquid separators is collected in storage tank 50. The liquid material withdrawn from tank 50 in line 52 is passed through a suitable drying trap, 54, and then split into two streams. A portion of the dried material is employed as reflux in line 34; and another portion is passed in line 56 to the product distillation purification system 60.

In the distillation purification system, crude chlorinated products, viz., $CH_2Cl_2$, $CHCl_3$ and $CCl_4$ are separated in line 61 from unreacted methyl chloride which is recycled via line 62. When higher yields of chloroform are desired, methylene chloride is also recycled to the reactor for further chlorination.

Referring once again to the partial condensation zone, it is important for the purposes of the present invention that such partial condensation is carried out under elevated pressure conditions which will, of course, be slightly lower than the pressure in the chlorination zone. A suitable low temperature is maintained at terminal condenser 44. Substantially anhydrous conditions are maintained throughout the partial condensation zone such that the vapor stream issuing from separator 45 in line 66 comprises substantially anhydrous hydrogen chloride under an elevated pressure having a major part of the $CH_3Cl$ and essentially all of the $CH_2Cl_2$, $CHCl_3$ and $CCl_4$ removed therefrom. In order to provide a suitable feed for a methanol hydrochlorination reactor, the exit conditions from the partial condensation zone are preferably maintained at a pressure between about 50 and about 200 psig and a temperature between about −25° and 0°C.

Substantially anhydrous hydrogen chloride admixed with a small percentage of methyl chloride in line 66 is admixed with methanol vapor from line 68 and introduced to a suitable methanol hydrochlorination reactor 70 for the production of methyl chloride. The hydrochlorination reaction is preferably effected in the presence of a catalyst. A most preferred catalytic material for use in conjunction with the integrated process of the present invention comprises solid activated alumina although solid or solutions of zinc chloride, as well as other catalysts known for carrying out this reaction, can be employed in the process of this invention. Methanol hydrochlorination is well known, for example, see U.S. Pat. No. 1,834,089, and French Pat. No. 1,471,895.

A vaporous effluent is recovered from zone 70 in line 72 comprising methyl chloride, hydrogen chloride and water. The effluent is then passed to a recovery system 74 which separates methyl chloride produced from the water of reaction. Water of reaction is removed and passed to waste containing small amounts of unreacted methyl alcohol, dimethyl ether, and unreacted or excess hydrogen chloride through line 75. Methyl chloride product and excess hydrogen chloride vapor saturated with water is withdrawn from the recovery system through line 82 and passed to drying zone 90. A preferable drying zone comprises a multiplate column irrigated counter currently with concentrated sulfuric acid. Concentrated sulfuric acid contacting also removes dimethyl ether impurities to a desired minimum level. The dried methyl chloride and hydrogen chloride containing stream in line 91 is treated in a refrigerated condenser 92 to separate methyl chloride liquid in line 94. The desired amount of methyl chloride is fed through line 94 for utilization in chlorination reactor 20. Liquid methyl chloride (crude, technical grade) is withdrawn from line 94 and purified in a conventional manner to provide technical grade methyl chloride. Vaporous methyl chloride containing some hydrogen chloride, alternatively, can be removed from line 91 to a compressor (not shown) which then pumps the crude methyl chloride vapor directly to the chlorination reactor 20 vapor feed mixing inlet header. This alternative procedure avoids refrigeration duty in low temperature condenser 92 and subsequent re-evaporation of the crude methyl chloride being recycled to the chlorination reactor 20. Substantially pure hydrogen chloride containing a small amount of methyl chloride is withdrawn in line 93 and can be further purified to yield a technically pure product.

It should also be pointed out that methyl chloride fed to reactor 20 can be added as a highly atomized liquid spray thereby permitting operating with higher chlorine to methyl chloride ratio in the single reactor system. The methyl chloride can also be introduced as a highly atomized liquid spray to both reactors of a two-series reactor system. When a higher yield of chloroform is desired, methylene chloride and methyl chloride are recycled to one or more reactors. For maximum thermodynamic economy, both the methylene chloride and the methyl chloride recycle are introduced to the reactor inlet or inlets as a highly atomized liquid spray, for example as described in U.S. Pat. No. 3,126,419.

Operating examples in accordance with the present invention are presented below.

EXAMPLE I

The following feed materials are intimately admixed and passed in line 16 to thermal chlorination reactor 20: 87.47 lb. mols per hr. of superheated chlorine vapor at 25°C.; 68.63 lb. mols per hr. methyl chloride vapor and 255.72 lb. mols per hr. recycle streams consisting of 186.4 lb. mols per hr. methyl chloride, 41.02 lb. mols per hr. hydrogen chloride, and 28.3 lb. mols per hr. methylene chloride. Reactor 20 is maintained at an operating pressure of about 110 psig and the maximum temperature attained in the reactor is 425°C. Reaction takes place in the reactor which provides a retention time of about 12 seconds. No free or unreacted chlorine is found in the reactor exit gas which is flowed to quench column 30. A liquid stream collected in tank 50 is introduced to quench tank 30 via line 34 in an upper portion thereof. The temperature at the bottom of quench vessel 30 is maintained at about 120°C. while the effluent vapor at the top of quench vessel 30 is at a temperature of about 100°C. Indirect water cooling is effected in condenser 40 to cool the vaporous material in line 38 to a temperature of about 40°C. Refrigerant cooling is effected to achieve a temperature of about 10°C. in condenser 42 and a temperature of about −12°C. in condenser 44. The terminal pressure of the gaseous material at the exit end of condenser 44 is about 100 psig.

The uncondensed material in line 66 has the following flow composition: 90.39 lb. mols per hr. hydrogen chloride; 13.56 lb. mols per hr. methyl chloride; and 0.01 lb. mols per hr. methylene chloride. Material in line 66 is admixed with 72.24 lb. mols per hr. of superheated methanol. The combined vapor is then fed to methanol hydrochlorination reactor 70 containing an activated alumina catalyst. Reaction heat is removed by a boiling heat transfer fluid contained in the jacketted side of reactor 70. In this example, the reaction effluent is reduced in temperature by passing through a conventional heat exchange recovery system 74. All of the water of reaction is removed from the process as about 22 wt % hydrochloric acid via line 75. The methyl chloride product, plus any excess hydrogen chloride vapor, saturated with water, is dried in multi plate drying column 90 which is counter currently irrigated with concentrated sulfuric acid. The dried methyl chloride-hydrogen chloride containing stream is passed to a low temperature condenser 92 in which methyl chloride is condensed and fed to the partial chlorination process in line 94. Any non-condensable hydrogen chloride present is withdrawn in line 93.

When maximum methylene chloride production is desirable, a low chlorine ratio and a single chlorination reactor, e.g., 20, is preferably employed with the excess methyl chloride acting as a diluent to control reaction temperature. When it is desirable to maximize the chloroform to methyl chloride product ratio via methyl chloride substitution chlorination, two reaction zones arranged in series can be employed as shown in U.S. Pat. No. 3,126,419. A diluent such as carbon tetrachloride or perchloroethylene can be employed when higher chlorinated products are desired in a one or a two reactor system.

Hydrogen chloride production resulting from the formation of chloroform or carbon tetrachloride during the substitution chlorination of methyl chloride can be recovered, controlled or removed in accordance with any one of the following preferable methods:

1. Hydrogen chloride can be recovered as a gaseous anhydrous HCl from the partial chlorination plant, e.g., from 66 line in the drawing. If liquid HCl is desired, a compressor is installed on the recovery system exit of the partial chlorination plant, e.g., between condenser 44 and separator 45, which compresses the HCl — $CH_3Cl$ vapor to at least about 150 psig. This gas is then cooled and fed to a fractionation column which, with benefit of a refrigerated reflux condenser returns liquid HCl reflux under at least about 150 psig to the top of the fractionator. The fractionator is, thus, (with sufficient sieve trays above the feed point) made capable of delivering substantially pure HCl overhead. By providing sufficient trays below the feed point the fractionator can produce a bottoms product of essentially pure $CH_3Cl$ for return to the proper point in the partial chlorination process, e.g., 60 or 62.

2. By installing a refrigerated $CCl_4$ (or $C_2Cl_4$) absorption system on the exit of the recovery system, (line 66) of the partial chlorination plant, it is also possible to obtain high quality hydrogen chloride off gas from the partial chlorination plant. The $CCl_4$ (or $C_2Cl_4$) underflow from the absorption column, containing $CH_3Cl$, and some HCl is then fed to a multiplate stripping column whereby HCl and $CH_3Cl$ can be removed as overhead product and returned to the chlorination reactor. Lean $CCl_4$ (or $C_2Cl_4$) underflow is watercooled, then refrigerant cooled and returned to the absorber.

3. Hydrogen chloride resulting from the production of chloroform or carbon tetrachloride in the partial chlorination process can be employed in the methanol hydrochlorination process to produce excess methyl chloride, thereby keeping the overall HCl production in balance.

4. Hydrogen chloride resulting from the production of chloroform or carbon tetrachloride in the partial chlorination process can be allowed to flow through the methanol hydrochlorination plant unreacted. It can then be removed as follows:
   a. By compression and fractionation as described in Item 1 above. In this case the compressor and fractionator is located in the recovery system of the methanol hydrochlorination following the sulfuric acid drying column 90.
   b. By refrigerated $CCl_4$ or $C_2Cl_4$ scrubbing which, in this case, is located in the recovery system of the methanol hydrochlorination following the sulfuric acid drying column 90.

In all above cases, separation of hydrogen chloride is effected in high quality and under anhydrous conditions.

EXAMPLE II

The feed materials and equipment as described in Example I are the same up to stream 66. The material in line 66 is admixed with methane and air or oxygen. This combined vapor is then fed to a methane oxychlorination reaction system such as is described in British Pat. No. 587,969 to produce additional methylene chloride, chloroform and carbon tetrachloride from the by-product HCl.

EXAMPLE III

The feed materials for this example are the same as for Example I. The equipment and operations are also the same up to stream 66. At this point, the uncondensed material with the composition 90.39 lbs. mols per hr. hydrogen chloride; 13.56 lb. mols per hr. methyl chloride and 0.01 lb. mols per hr. methylene chloride is fed to a compressor which compresses the mixture to 150 psig. This gas is then cooled and fed to a fractionation column. A refrigerated reflux condenser returns liquid HCl reflux to the top of the column. An overhead stream which comprises substantially anhydrous, purified hydrogen chloride composed of 89.49 lb. mols per hr. HCl and 0.009 lb. mols per hr. $CH_3Cl$ is withdrawn from the fractionation column. Such overhead stream of substantially anhydrous, purified hydrogen chloride is intimately admixed with ethylene and air or oxygen and fed to an ethylene oxychlorination reaction system as described in Canadian Pat. No. 517,009. The stream from the bottoms of the fractionation column composed of 0.90 mols per hr. HCl, 13.20 mols per hr. $CH_3Cl$ and 0.01 mols per hr. $CH_2Cl_2$ is recycled to the partial chlorination process in line 94.

EXAMPLE IV

The feed materials for this example are the same as for Example I. The equipment and operations are also the same up to stream 66. At this point, the uncondensed material with the composition 90.39 lb. mols per hr. hydrogen chloride; 13.56 lb. mols per hr. methyl chloride and 0.01 lb. mols per hr. methylene chloride is fed to a compressor which compresses the mixture to 150 psig. This gas is then cooled and fed to a fractionation column. A refrigerated reflux condenser returns liquid HCl reflux to the top of the column. An overhead product stream composed of 89.49 lb. mols per hr. HCl and 0.009 lb. mols per hr. $CH_3Cl$ is withdrawn from the fractionation column and is intimately admixed with ethane and air or oxygen and fed to an ethane oxychlorination reaction system which produces principally ethyl chloride and dichloroethanes, as in British Pat. No. 938,096. By variation of $C_2H_6$:HCl ratio, this process produces trichloroethylene and perchloroethylene in varying amounts.

EXAMPLE V

The feed materials for this example are the same as for Example I. The equipment and operations are also the same up to stream 66. At this point, the uncondensed material with the composition 90.39 lb. mols per hr. hydrogen chloride; 13.56 lb. mols per hr. methyl chloride and 0.01 lb. mols per hr. methylene chloride is fed to a compressor which compresses the mixture to 150 psig. This gas is then cooled and fed to a fractionation column. A refrigerated reflux condenser returns liquid HCl reflux to the top of the column. An overhead product stream composed of 89.49 lb. mols per hr. HCl and 0.009 lb. mols per hr. $CH_3Cl$ is withdrawn from the fractionation column and is intimately admixed with ethylene dichloride and air or oxygen and fed to an ethylene oxychlorination reaction system for production of trichloroethylene and perchloroethylene as described; for example, as a second stage reactor in British Pat. No. 904,405.

EXAMPLE VI

The feed materials for this example are the same as for Example I. The equipment and operations are also the same up to stream 66. At this point, the uncondensed material with the composition 90.39 lb. mols per hr. hydrogen chloride; 13.56 lb. mols per hr. methyl chloride and 0.01 mols per hr. methylene chloride is fed to a compressor which compresses the mixture to 150 psig. This gas is then cooled and fed to a fractionation column. A refrigerated reflux condenser returns liquid HCl reflux to the top of the column. An overhead product stream composed of 89.49 lb. mols per hr. HCl and 0.009 lb. mols per hr. $CH_3Cl$ is withdrawn from the fractionation column and is intimately admixed with benzene and air or oxygen and fed to a benzene oxychlorination reaction system according to the Raschig (Prahl) process described in British Pat. No. 362,817 or as described in Chem. and Met. Engr. 47, No. 11, Pages 770–775 (1940). Mainly monochlorobenzene is formed with good hydrogen chloride utilization and only minor amounts of polychlorinated benzene by-products are formed.

EXAMPLE VII

The feed materials for this example are the same as for Example I. The equipment and operations are also the same up to stream 66. At this point, the uncondensed material with the composition 90.39 lb. mols per hr. hydrogen chloride; 13.56 lb. mols per hr. methyl chloride and 0.01 lb. mols per hr. methylene chloride is fed to a compressor which compresses the mixture to 150 psig. This gas is then cooled and fed to a fractionation column. A refrigerated reflux condenser returns liquid HCl reflux to the top of the column. An overhead product stream composed of 89.49 lb. mols per hr. HCl and 0.009 lb. mols per hr. $CH_3Cl$ is withdrawn from the fractionation column and is intimately admixed with acetylene and air or oxygen and fed to an acetylene oxychlorination reaction system as described in British Pat. No. 1,090,783. Products of the reaction are dichloroethylene, trichloroethylene and some more highly chlorinated ethylenes or ethanes. Steam and inert gases may also be introduced with the feed raw materials in such an acetylene oxychlorination process to improve yields by ensuring the optimum reaction temperature.

EXAMPLE VIII

The feed materials for this example are the same as for Example I. The equipment and operations are also the same up to stream 66. At this point, the uncondensed material with the composition 90.39 lb. mols per hr. hydrogen chloride; 13.56 lb. mols per hr. methyl chloride and 0.01 lb. mols per hr. methylene chloride is fed to a compressor which compresses the mixture to 150 psig. This gas is then cooled and fed to a fractionation column. A refrigerated reflux condenser returns liquid HCl reflux to the top of the column. An overhead product stream composed of 89.49 lb. mols per hr. HCl and 0.009 lb. mols per hr. $CH_3Cl$ is withdrawn from the fractionation column and is intimately admixed with ethylene and fed to a liquid or vapor phase hydrochlorination reactor, containing an active catalyst, for production of ethyl chloride. A typical preferred liquid phase ethyl chloride process is described in Canadian Pat. No. 448,020.

EXAMPLE IX

The feed materials or this example are the same as for Example I. The equipment and operations are also the same up to stream 66. At this point, the uncondensed material with the composition 90.39 lb. mols per hr. hydrogen chloride; 13.56 lb. mols per hr. methyl chloride and 0.01 lb. mols per hr. methylene chloride is fed to a compressor which compresses the mixture to 150 psig. This gas is then cooled and fed to a fractionation column. A refrigerated reflux condenser returns liquid HCl reflux to the top of the column. An overhead product stream composed of 89.49 lb. mols per hr. HCl and 0.009 lb. mols per hr. $CH_3Cl$ is withdrawn from the fractionation column and is fed to a toluene chloromethylation process containing toluene and paraformaldehyde in the presence of zinc chloride as described in Blane, Bull. Soc. chim., 1923, 33, 313. In this reaction the chloromethyl group is introduced to the toluene ring in high yield and the reaction can be carried out in either a batch or continuous manner.

EXAMPLE X

This example considers the case in which the first zone comprises methane partial chlorination and the hydrogen chloride consuming zone comprises a methane oxychlorination reaction zone.

The following feed materials are intimately admixed and passed in line 16 to reactor zone 20: 44.40 lb. mols per hr. superheated chlorine vapor at 25°C.; 18.67 lb. mols per hr. methane and recycle stream consisting of 37.48 lb. mols per hr. methane, 6.22 lb. mols per hr. inerts, 18.70 lb. mols per hr. $CH_3Cl$ and 0.43 lb. mols per hr. $CH_2Cl_2$. Reactor 20 consists of two thermal chlorination reactors in series. Reactor 20 is maintained at an operating pressure of about 40 psig and the maximum reactor temperature attained is 425°C. Reaction takes place in the reactor which provides a retention time of about 12 seconds. No free or unreacted chlorine is found in the reactor exit gas which is flowed to quench column 30. A liquid stream collected in tank 50 is introduced to quench tank 30 via line 34 in an upper portion thereof. The temperature at the bottom of quench vessel 30 is about 120°C. while the effluent vapor at the top of quench vessel 30 is at a temperature of about 100°C. Indirect water cooling is effected in condenser 40 to cool the vaporous material in line 38 to a temperature of about 40°C. Refrigerant cooling is effected to a temperature of about 10°C. in condenser 42 and a temperature of about −25°C. in condenser 44. The terminal pressure of the gaseous material at the exit end of condenser 44 is about 37 psig.

The uncondensed material in line 66 has the following flow compositions: 44.90 lb. mols per hr. hydrogen chloride; 18.91 lb. mols per hr. methyl chloride; 0.43 lb. mols per hr. methylene chloride; 6.29 lb. mols per hr. inerts and 37.90 lb. mols per hr. methane. The material in line 66 is admixed with 28.5 lb. mols per hr. chlorine.

This combined vapor is then fed to a methane oxychlorination reactor maintained under conditions to produce maximum methylene chloride.

It is much more economical, from the standpoint of equipment and operating costs, to purify HCl under anhydrous conditions than to involve a water or weak acid absorption-stripping method for the removal of unreacted hydrocarbon or chlorohydrocarbons, as described in the foregoing examples.

Many modifications and alterations will become apparent to those skilled in the art from the foregoing description of the invention which should be limited only by the claims.

We claim:

1. In a process of carrying out the vapor phase, thermal substitution chlorination of methyl chloride thereby producing a vaporous effluent comprising chlorine substituted materials in admixture with hydrogen chloride, the improvement comprising conducting the reaction in a first zone under substantially anhydrous conditions at a temperature between about 350° and 500°C. and under an elevated pressure between about 50 and about 200 psig., withdrawing said effluent and passing same to a partial condensation zone, maintained under an elevated pressure between about 50 and about 200 psig and low terminal temperature, to condense chlorine substituted materials and to provide a gas stream containing substantially anhydrous hydrogen chloride and a small percentage of chlorine substituted hydrocarbons.

2. The process of claim 1 wherein the effluent from the first zone is passed to a quenching zone to reduce the temperature of said effluent before passing to the partial condensation zone.

3. The process of claim 1 in which said partial condensation zone is maintained at a terminal temperature between about minus 25°C. and about 0°C.

4. The process of claim 2 in which said partial condensation zone is maintained at a temperature between about minus 25°C. and 0°C.

5. In a process of carrying out the vapor phase, thermal substitution chlorination of methyl chloride thereby producing a vaporous effluent comprising chlorine substituted materials in admixture with hydrogen chloride, the improvement comprising conducting the reaction in a first zone under substantially anhydrous conditions at a temperature between about 350°C. and 500°C. and a pressure between about 50 psig and about 200 psig, passing said effluent to a quenching zone and then to a partial condensation zone maintained at a pressure between about 50 psig and about 200 psig and a relatively low terminal temperature to separate chlorine substituted materials from a substantially anhydrous gas stream containing hydrogen chloride, passing said gas stream containing hydrogen chloride, at a pressure between about 50 psig and about 200 psig, to a separation zone to separate additional chlorine substituted materials from said gas stream to produce substantially anhydrous, purified hydrogen chloride.

6. The process of claim 5 in which substantially anhydrous gaseous hydrogen chloride withdrawn from said partial condensation zone is compressed, if required, to a pressure of at least about 150 psig., cooled and then fractioned at a pressure of at least about 150 psig. to separate additional chlorinated materials and form substantially anhydrous, purified hydrogen chloride.

7. The process of claim 5 wherein the terminal temperature of the partial condensation zone is between about minus 25°C. and 0°C.

8. The process of claim 5 wherein at least a portion of the anhydrous gas stream from the partial condensation zone is contacted with a chilled chlorine-carbon compound selected from the group consisting of carbon tetrachloride and perchloroethylene at a pressure between about 50 psig., and about 200 psig. to produce an anhydrous hydrogen chloride substantially free of chlorine substituted hydrocarbon materials.

* * * * *